US00PP31810P2

(12) United States Plant Patent
Geibel

(10) Patent No.: US PP31,810 P2
(45) Date of Patent: May 26, 2020

(54) ***PELARGONIUM* PLANT NAMED 'SWERED'**

(50) Latin Name: ***Pelargonium* x *hortorum***
Varietal Denomination: Swered

(71) Applicant: Martin Geibel, Dresden (DE)

(72) Inventor: Martin Geibel, Dresden (DE)

(73) Assignee: Elsner Jungpflangen Gbr, Dresden (DE)

( * ) Notice: Subject to any disclaimer, the term of this patent is extended or adjusted under 35 U.S.C. 154(b) by 0 days.

(21) Appl. No.: 16/501,548

(22) Filed: Apr. 29, 2019

(51) Int. Cl.
*A01H 5/02* (2018.01)
*A01H 6/42* (2018.01)

(52) U.S. Cl.
USPC ..... Plt./325
CPC ..... *A01H 6/42* (2018.05)

(58) Field of Classification Search
USPC ..... Plt./325, 330
CPC ..... A01H 5/02
See application file for complete search history.

*Primary Examiner* — Kent L Bell
(74) *Attorney, Agent, or Firm* — C. A. Whealy

(57) ABSTRACT

A new and distinct Zonal Geranium plant named 'Swered', characterized by its upright and uniformly rounded plant habit; vigorous growth habit; freely basal branching habit; dark green-colored leaves; early and freely flowering habit; and red-colored semi-double flowers with light purplish pink and white-colored centers that are held above the foliar plane on strong peduncles.

1 Drawing Sheet

Botanical designation: *Pelargonium* x *hortorum.*
Cultivar denomination: 'SWERED'.

BACKGROUND OF THE INVENTION

The present invention relates to a new and distinct cultivar of Zonal Geranium plant, botanically known as *Pelargonium* x *hortorum*, and hereinafter referred to by the cultivar name 'Swered'.

The new Zonal Geranium plant is a product of a planned breeding program conducted by the Inventor in Dresden, Germany. The objective of the breeding program is to develop new early-flowering Zonal Geranium plants with dark green-colored leaves and numerous attractive flowers.

The new Zonal Geranium plant originated from a cross-pollination made by the Inventor of two unidentified proprietary selections of *Pelargonium* x *hortorum*, not patented, during the summer of 2013. Seed was collected from a number of potential parent plants, combined and sown. The new Zonal Geranium plant was discovered and selected by the Inventor as a single flowering plant from within the progeny of the stated mass cross-pollination in a controlled greenhouse environment in Dresden, Germany during the spring of 2014.

Asexual reproduction of the new Zonal Geranium plant by vegetative terminal cuttings in a controlled greenhouse environment in Dresden, Germany since January, 2015 has shown that the unique features of this new Zonal Geranium plant are stable and reproduced true to type in successive generations.

SUMMARY OF THE INVENTION

Plants of the new Zonal Geranium have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Swered'. These characteristics in combination distinguish 'Swered' as a new and distinct Zonal Geranium plant:

1. Upright and uniformly rounded plant habit.
2. Vigorous growth habit.
3. Freely basal branching habit.
4. Dark green-colored leaves.
5. Early and freely flowering habit.
6. Red-colored semi-double flowers with light purplish pink and white-colored centers that are held above the foliar plane on strong peduncles.

Plants of the new Zonal Geranium can be compared to plants of the *Pelargonium* x *hortorum* 'Pacswibu', disclosed in U.S. Plant Pat. No. 28,106. In side-by-side comparisons, plants of the new Zonal Geranium differ from plants of 'Pacswibu' in the following characteristics:

1. Plants of the new Zonal Geranium are larger, more vigorous and grow faster than plants of 'Pacswibu'.
2. Plants of the new Zonal Geranium have larger and slightly lighter green-colored leaves than plants of 'Pacswibu'.
3. Plants of the new Zonal Geranium are more freely flowering than plants of 'Pacswibu'.
4. Plants of the new Zonal Geranium have larger umbels than plants of 'Pacswibu'.
5. Plants of the new Zonal Geranium have longer peduncles than plants of 'Pacswibu'.

BRIEF DESCRIPTION OF THE PHOTOGRAPH

The accompanying colored photograph illustrates the overall appearance of the new Zonal Geranium plant showing the colors as true as it is reasonably possible to obtain in colored reproductions of this type. Colors in the photograph may differ slightly from the color values cited in the detailed botanical description which accurately describe the colors of the new Zonal Geranium plant.

The photograph comprises a side perspective view of a typical flowering plant of 'Swered' grown in a container.

DETAILED BOTANICAL DESCRIPTION

The aforementioned photograph and following observations, measurements and values describe plants grown in 19-cm containers during the winter, spring and summer in a glass-covered greenhouse in Dresden, Germany and under cultural practices typical of commercial Zonal Geranium production. During the production of the plants, day temperatures averaged 18° C., night temperatures averaged 16° C. and light levels ranged from 15 kilolux to 100 kilolux. Plants were four months old when the photograph was taken and nine months old when the detailed description was taken. In the detailed description, color references are made to The Royal Horticultural Society Colour Chart, 1995 Edition, except where general terms of ordinary dictionary significance are used.

Botanical classification: *Pelargonium* x *hortorum* 'Swered'.

Parentage:

*Female, or seed, parent*.—Unidentified proprietary selection of *Pelargonium* x *hortorum*, not patented.

*Male or pollen parent*.—Unidentified proprietary selection of *Pelargonium* x *hortorum*, not patented.

Propagation:

*Type*.—By vegetative terminal cuttings.

*Time to initiate roots, summer*.—About 18 days at temperatures about 20° C.

*Time to initiate roots, winter*.—About 22 days at temperatures about 20° C.

*Time to produce a rooted young plant, summer*.—About four weeks at temperatures about 20° C.

*Time to produce a rooted young plant, winter*.—About four weeks at temperatures about 18° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Upright and uniformly rounded plant habit; inverted triangle; densely foliated; vigorous growth habit; rapid growth rate; freely basal branching habit with about 15 lateral branches developing per plant; pinching is typically not required.

*Plant height, to top of umbels*.—About 34 cm.

*Plant height, to top of foliar plane*.—About 24 cm.

*Plant width*.—About 55 cm.

*Lateral branches*.—Length: About 12 cm. Diameter: About 8 mm. Internode length: About 1.5 cm. Texture: Moderately pubescent. Color: Close to 146C.

Leaf description:

*Arrangement*.—Opposite; simple.

*Length*.—About 6.2 cm.

*Width*.—About 9.3 cm.

*Shape*.—Rounded; roughly reniform.

*Apex*.—Rounded.

*Base*.—Cordate, open.

*Margin*.—Crenate.

*Venation pattern*.—Palmate.

*Texture, upper and lower surfaces*.—Slightly pubescent; coriaceous.

*Color*.—Developing and fully expanded leaves, upper surface: Close to 137A; venation, close to 137A. Developing and fully expanded leaves, lower surface: Close to 147B; venation, close to 146C. Zonation pattern: Not discernible.

*Petioles*.—Length: About 7.5 cm. Diameter: About 2 mm. Texture, upper and lower surfaces: Pubescent; rough. Color, upper and lower surfaces: Close to 146B.

Flower description:

*Flower arrangement and flowering habit*.—Semi-double flowers arranged in roughly hemispherical umbels arising from apical leaf axils; umbels displayed above the foliar plane on strong peduncles; flowers face upright to outwardly; freely flowering habit with about two flower buds and about 21 open flowers per umbel and about 30 umbels developing per plant during the flowering season.

*Fragrance*.—None detected.

*Flowering season*.—Early flowering habit; plants begin flowering about 75 days after planting; in the garden in Germany, flowering begins in April and continues until frost in the autumn.

*Flower longevity*.—Flowers last about six to ten days on the plant; umbels last about three to four weeks on the plant; flowers persistent.

*Umbel height*.—About 7 cm.

*Umbel diameter*.—About 12.5 cm.

*Flower diameter*.—About 5 cm.

*Flower depth (height)*.—About 2 cm.

*Flower buds*.—Length: About 1 cm. Diameter: About 6 mm. Shape: Elliptical. Color: Close to 144A.

*Petals*.—Quantity per flower: About seven; petals imbricate. Length, upper petals: About 2.7 cm. Length, lower petals: About 2.6 cm. Width, upper petals: About 2.2 cm. Width, lower petals: About 2.4 cm. Shape: Roughly spatulate. Apex: Rounded. Base: Cuneate. Margin: Entire. Texture, upper and lower surfaces: Smooth, glabrous; velvety. Color: When opening and fully opened, upper surface: Close to 45B; towards the base, close to 73B; at the base, close to 155D; venation, close to 45B; color does not change with development. When opening and fully opened, lower surface: Close to 73B; towards the base, close to 155D; venation, close to 66B; color does not change with development.

*Petaloids*.—To date, petaloid development has not been observed on plants of the new Zonal Geranium.

*Sepals*.—Quantity per flower: Five arranged in a single whorl. Length: About 1 cm. Width: About 3 mm. Shape: Lanceolate. Apex: Acute. Margin: Entire. Texture, upper surface: Smooth, glabrous. Texture, lower surface: Pubescent. Color, upper and lower surfaces: Close to 144A.

*Peduncles (umbel stems)*.—Length: About 16 cm. Diameter: About 4 mm. Strength: Strong. Angle: Mostly upright. Texture: Moderately pubescent. Color: Close to 144A.

*Pedicels* (*individual flower stems*).—Length: About 3.5 cm. Diameter: About 2 mm. Strength: Moderately strong; flexible. Texture: Moderately pubescent. Color: Close to 144A.

*Reproductive organs*.—Androecium: Stamen quantity per flower: About eleven. Anther length: About 2 mm. Anther shape: Tubular. Anther color: Close to 67A. Pollen amount: Abundant. Pollen color: Close to 169A. Gynoecium: Pistil quantity per flower: One. Pistil length: About 8 mm. Stigma shape: Five or six-parted. Stigma color: Close to 42A. Style length: About 2 mm. Style color: Close to 42A. Ovary color: Close to 147C. Seeds and fruits: To date, seed and fruit development have not been observed on plants of the new Zonal Geranium.

Pathogen & pest resistance: To date, plants of the new Zonal Geranium have not been observed to be resistant to pathogens and pests common to Zonal Geranium plants.

Temperature tolerance: Plants of the new Zonal Geranium have been observed to tolerate temperatures ranging from about 1° C. to about 35° C. to 40° C.

It is claimed:

1. A new and distinct Zonal Geranium plant named 'Swered' as illustrated and described.

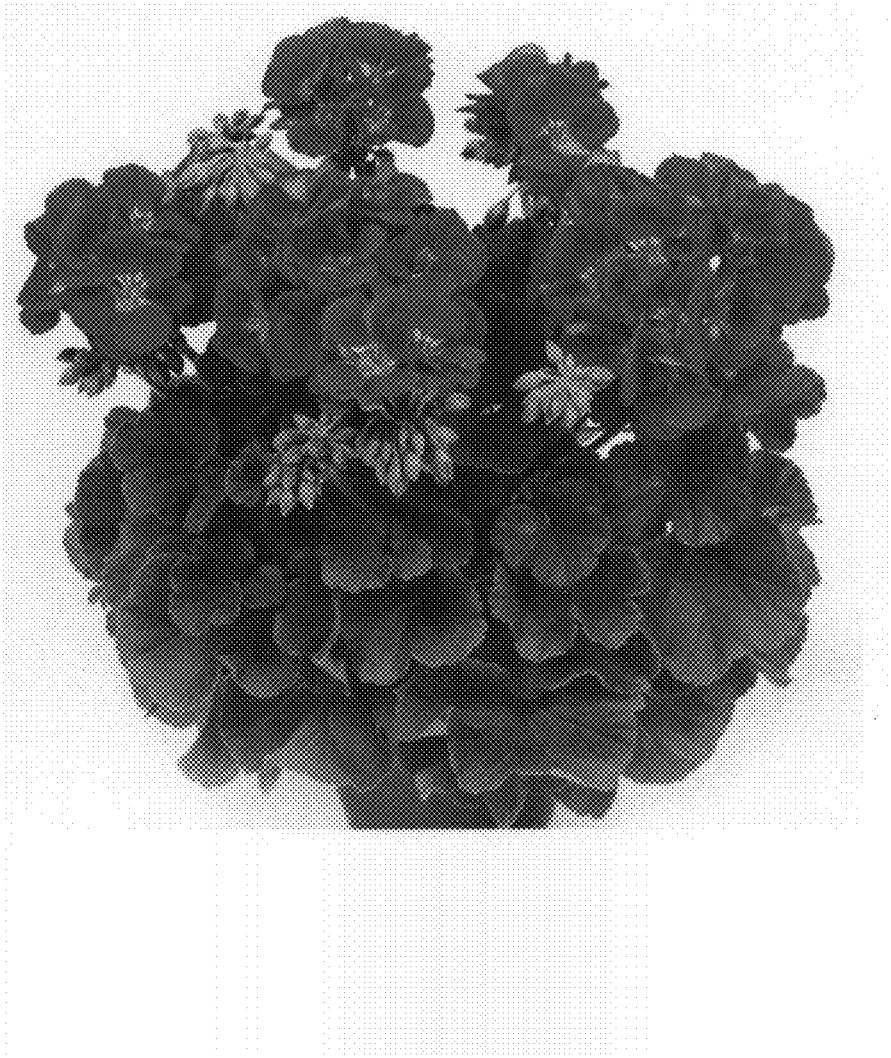

* * * * *